(12) United States Patent
Edwards

(10) Patent No.: US 6,514,898 B2
(45) Date of Patent: Feb. 4, 2003

(54) PROCESS OF PREPARING A FLUID RARE EARTH ALKOXYLATION CATALYST

(75) Inventor: Charles Lee Edwards, Houston, TX (US)

(73) Assignee: Shell Oil Company, Houston, TX (US)

( * ) Notice: Subject to any disclaimer, the term of this patent is extended or adjusted under 35 U.S.C. 154(b) by 4 days.

(21) Appl. No.: 09/737,989

(22) Filed: Dec. 15, 2000

(65) Prior Publication Data

US 2002/0142913 A1 Oct. 3, 2002

(51) Int. Cl.[7] .......................... B01J 27/14; B01J 23/00; C01B 25/00; C01B 15/16
(52) U.S. Cl. ................. 502/208; 502/303; 423/299; 423/305; 987/300
(58) Field of Search ................ 502/208, 303; 423/299, 305; 987/300

(56) References Cited

U.S. PATENT DOCUMENTS

| | | | |
|---|---|---|---|
| 3,838,182 A | | 9/1974 | Kahl et al. |
| 4,002,725 A | * | 1/1977 | Bridenbaugh et al. ...... 423/263 |
| 4,098,818 A | | 7/1978 | Krummel et al. ....... 260/535 R |
| 5,057,627 A | * | 10/1991 | Edwards ...................... 568/618 |
| 5,057,628 A | * | 10/1991 | Edwards et al. ............. 568/618 |
| 5,059,719 A | * | 10/1991 | Edwards ...................... 568/618 |
| 5,102,849 A | * | 4/1992 | Kemp et al. ................. 502/214 |
| 5,112,788 A | | 5/1992 | King |
| 5,118,870 A | * | 6/1992 | Kemp .......................... 568/618 |
| 5,208,199 A | * | 5/1993 | Kemp .......................... 502/208 |
| 5,210,325 A | * | 5/1993 | Kemp et al. ................. 568/618 |

FOREIGN PATENT DOCUMENTS

| | | | |
|---|---|---|---|
| GB | 1462134 | 3/1975 | .......... C07C/43/04 |
| GB | 1553561 | 7/1976 | .......... C11D/10/02 |

OTHER PUBLICATIONS

Derwent Publications Research Disclosure No. 194,010, Jun. 1980, pp. 219–222.

* cited by examiner

Primary Examiner—Mark L. Bell
Assistant Examiner—Patricia L. Hailey

(57) ABSTRACT

A process to prepare an improved fluid rare earth phosphate catalyst composition useful in preparing alkylene oxide adducts of organic compounds having active hydrogen atoms is provided. The catalyst is prepared by dissolving a rare earth salt in a $C_9$–$C_{30}$ active hydrogen containing organic compound and then adding phosphoric acid to the organic compound rare earth mixture.

11 Claims, No Drawings

PROCESS OF PREPARING A FLUID RARE EARTH ALKOXYLATION CATALYST

This invention relates to a process of preparing a rare earth catalyst useful in an alkoxylation process.

BACKGROUND OF THE INVENTION

A large variety of products useful, for instance, as non-ionic surfactants, wetting and emulsifying agents, solvent, and chemical intermediates, are prepared by the addition reaction (alkoxylation reaction) of alkylene oxides (epoxides) with organic compounds having one or more active hydrogen atoms. For example, particular mention may be made of the alkanol ethoxylates and alkyl-substituted phenol ethoxylates prepared by the reaction of ethylene oxide with aliphatic alcohols or substituted phenols of about 6 to 30 carbon atoms. Such ethoxylates, and to a lesser extent corresponding propoxylates and compounds containing mixed oxyethylene and oxypropylene groups, are widely employed as nonionic detergent components of commercial cleaning formulations for use in industry and in the home. As another example, the addition reaction of propylene oxide with polyols provides intermediates for the preparation of polyurethane products.

An illustration of the preparation of an alkanol ethoxylate (represented by formula III below) by addition of a number (n) of ethylene oxide molecules (formula 11) to a single alkanol molecule (formula I) is presented by the equation

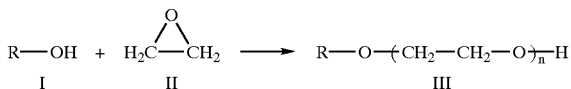

The present invention particularly relates to an alkoxylation reaction catalyzed by the phosphate salts of one or more of the rare earth elements.

Alkylene oxide addition reactions are known to produce a product mixture of various alkoxylate molecules having different numbers of alkylene oxide adducts (oxyalkylene adducts), e.g., having different values for the adduct number n in formula III above. The adduct number is a factor which in many respects controls the properties of the alkoxylate molecule, and efforts are made to tailor the average adduct number of a product and/or the distribution of adduct numbers within a product to the product's intended service.

It is known that alcohol alkoxylate products having a narrow range alkylene oxide adduct distribution are preferred for use in certain detergent formulations (Great Britain Patent No. 1,462,134; Derwent Publications Research Disclosure number 194,010). Narrow-range alcohol alkoxylates are also known to be particularly valuable as chemical intermediates in the synthesis of certain carboxylated alkyl polyethers (U.S. Pat. No. 4,098,818) and of certain alkyl ether sulfates (Great Britain Patent No. 1,553,561).

U.S. Pat. No. 5,057,627 describes an alkoxylation process catalyzed phosphate salts of the rare earth elements. These catalysts were typically prepared by adding an aqueous solution of a rare earth compound such as lanthanum chloride to an aqueous sodium orthophosphate or $H_3PO_4$ solution. The resulting catalyst was a solid powder that was stable with a long shelf-life. However, often the reaction mixture prepared by these catalysts lead to an increase in the viscosity of the mixture to 1000 centipoise or more. U.S. Pat. No. 5,057,627 also describes a process where an alkylphosphate is added to a lanthanum solution of 2-ethoxyethanol and NEODOL™ 23 Alcohol. Such a system may produce a lower viscosity mixture, however, these catalysts have a slow reaction time.

It is desirable to prepare a catalyst that provides a low viscosity reaction system with faster reaction time.

SUMMARY OF THE INVENTION

A process for the preparation of a fluid rare earth phosphate catalyst composition comprising:

a) providing a rare earth salt soluble in $C_9$–$C_{30}$ active hydrogen containing organic compounds at a temperature of less than 120° C.;

b) adding and dissolving the rare earth salt in a $C_9$–$C_{30}$ active hydrogen containing organic compounds thereby producing a rare earth/organic solution; and c) adding phosphoric acid to the rare earth/organic solution in a rare earth to phosphoric acid molar ratio in the range of 0.7:1 to 1.3:1 thereby producing the fluid rare earth phosphate catalyst composition.

Further, processes for the preparation of alkylene oxide adducts of active hydrogen containing organic compounds are provided, comprising contacting an alkylene oxide reactant comprising one or more vicinal alkylene oxide with an active hydrogen containing reactant comprising one or more active hydrogen containing organic compounds in the presence of the fluid catalyst composition prepared by certain processes.

DESCRIPTION OF THE PREFERRED EMBODIMENTS

It has now been found that the alkoxylation reaction carried out in the presence of the rare earth phosphate catalyst composition prepared by the process of the invention, decreases reaction time and is easier to handle.

In the process of the invention, a fluid rare earth phosphate catalyst is prepared by the steps comprising a) providing a certain rare earth salt, b) adding and dissolving the rare earth salt in a $C_9$–$C_{30}$ active hydrogen containing organic compounds, preferably in a $C_9$–$C_{30}$ primary monohydric alkanol or alkylphenol, more preferably in a $C_9$–$C_{30}$ primary mono-hydric alkanol; then c) adding phosphoric acid to the rare earth/organic solution, or more preferably to the rare earth/alkanol solution. It has been surprisingly found that the desirable catalyst composition can be prepared in the $C_9$–$C_{30}$ active hydrogen containing organic compound without the presence of low molecular weight alcohol or alkoxides (carbon number of less than 8).

When the catalyst is prepared according to the invention, the rare earth phosphate is substantially uniformly dispersed in the alkanol having an average particle size of less than about 2 microns, more preferably medium diameter particles are less than about 1 micron. The catalyst composition comprising the dispersed rare earth phosphate salt and the alkanol has a viscosity of about less than 50 centipoise, and is fluid. The term "fluid" means having particles which easily move and change their relative position without a separation of the mass, and which readily yield to pressure.

As the terminology is used herein, the "rare earth" elements are those of atomic numbers 39 and 57 through 71, elements of the "lanthanum series" are those of atomic numbers 57 through 71; the "lanthanide" elements are those of atomic numbers 58 through 71. Traditionally, the lanthanum series has further been divided into the "cerium earth" group of atomic numbers 57 through 62, the "terbium earth" group of atomic numbers 63 through 66, and the "yttrium earth" group of atomic numbers 67 through 71 (so named not because yttrium is a member of the group, but because yttrium is found with these elements in nature).

In general terms, the catalyst for the process of the invention comprises one or more of the phosphate salts of the rare earth metals. In one preferred embodiment, the catalyst comprises one or more of the phosphate salts of the lanthanum series elements. In another embodiment, the catalyst comprises one or more of the phosphate salts of the lanthanide elements. In a further specific embodiment, the catalyst comprises one or more of the phosphate salts of the elements of the cerium earth group. In still another specific embodiment, the catalyst comprises a mixture of rare earth metal phosphate salts wherein the distribution of the rare earth elements substantially corresponds to that of a naturally occurring rare earth ore, for example, monazite, bastnasite, xenotime, gadolinite or euxenite.

The catalyst in a given application of this process suitably contains the phosphate salt(s) of either one or a mixture of the rare earth elements. In one respect, preference can be expressed for catalysts comprising in catalytically effective amount one or more of the phosphate salts of elements selected from the group comprising cerium, lanthanum, praseodymium, neodymium, yttrium, samarium, gadolinium, dysprosium, erbium, and ytterbium. In another respect, catalysts comprising a catalytically effective amount of one or more of the phosphate salts of the cerium earth group elements are particularly preferred, while catalysts comprising a catalytically effective amount of one ore more of the phosphate salts of elements selected from the group consisting of cerium and lanthanum are considered most preferred. In a further respect, preferred catalysts comprise a catalytically effective amount of one or more of the phosphate salts of lanthanum.

Natural mineral ores which serve as the commercial sources of the rare earth elements generally contain several of the elements. These ores are often refined without separating this mixture into distinct elements. For this reason, the use in the invention of mixtures of the phosphate salts of several rare earth elements may be preferred from the standpoint of availability and cost. Specific examples of suitable mixtures of rare earth elements include those known as bastnasite, monazite, xenotime, didymium, gadolinite and euxenite.

The rare earth salt useful to produce the fluid rare earth phosphate catalysts are soluble in the $C_9$–$C_{30}$ primary monohydric alkanol at a temperature of less than 120° C. Such rare earth salts can be, for example, halides, nitrates, or carboxylates of the rare earth elements. Some examples of salts include bromides, chlorides, nitrates, acetates, and octoates.

The rare earth salt is dissolved in the $C_9$–$C_{30}$ active hydrogen containing organic compound at temperatures in the range of ambient temperature up to 120° C. to provide a rare earth/organic solution. The rare earth salt may optionally be dissolved in water prior to addition to the organic compound, or preferably alkanol, to dissolve the rare earth salt faster. However, this is not necessary, and it is preferably desirable to have as little water as possible in the rare earth/alkanol solution.

To this rare earth/organic solution, phosphoric acid is added slowly in a rare earth to phosphoric acid molar ratio in the range of from 0.7:1, more preferably from 0.9:1, to 1.3:1, more preferably from 1.1:1 to produce the fluid rare earth phosphate catalyst composition. The phosphoric acid can be in any form including concentrated form or in an aqueous solution. The concentration is preferably in the range of 50 percent to 80 percent by weight in aqueous solution.

The fluid rare earth phosphate catalyst can be optionally treated with a base in an amount to bring the pH of the catalyst composition in the range of 5–8 as long as the base does not interfere with the alkoxylation reaction. Such base typically does not contain a Group 1 or Group 2 elements of the Periodic Table, such as $Na^+$, $K^+$, $Cs^+$, $Ba^+$, $Mg^+$, $Ca^+$, etc. Ammonium hydroxide is particularly preferred.

The resulting mixture should preferably be dried to a moisture content of less than 200 ppm prior to carrying out the alkoxylation reaction to minimize polyalkylene oxide polymer formation.

The rare earth phosphate salt catalyst compounds are suitably characterized by the formula $(L_p\text{-}(PO_4)_q)_n$ wherein L is a rare earth element. As is well recognized in the art, the phosphate salts of the rare earth elements principally comprises rare earth elements in the trivalent states and have the formula $LPO_4$. However, the invention is also intended to encompass divalent metal salts and tetravalent metal salts, in which case the subscripts p and q satisfy the relevant valency relationships, that is, when L is divalent p is 3 and q is 2, and when L is tetravalent p is 3 and q is 4. It is to be expected that generally the phosphate salt catalyst as prepared and as used in the invention will consist essentially of compounds of the formula LPO4. Further, the phosphate salt of rare earth elements may be in a dimer or trimeric form in which case n is 2 or 3 respectively.

In addition to a catalytically effective amount of the rare earth element compounds, the catalyst for the process of the invention may also suitably contain other substances, including both those which may be introduced into the process as impurities in the phosphate salt catalyst as well as those which may be added to promote or modify catalyst activity.

The one or more of the phosphate salts of the rare earth elements are present in the reaction mixtures in a catalytically effective amount, i.e., an amount sufficient to promote the alkoxylation reaction or influence the alkylene oxide adduct distribution of the product. Although a specific quantity of catalyst is not critical to the invention, preference may be expressed for use of the catalyst in an amount of at least about 0.01 percent by weight (% w), while an amount between about 0.02 and 5% w is considered more preferred and an amount between about 0.1 and 2% w is considered most preferred for typical embodiments. These percentages are in terms of the weight of rare earth metal ions in the process mixture relative to the weight of active hydrogen containing compounds in that mixture. Substantially greater quantities of catalyst, e.g., up to about 10% w or more, are also very suitable. As a rule, the higher the desired average alkylene oxide adduct number of the alkoxylate product and the higher the desired rate of reaction, the greater the required quantity of catalyst.

The invention is preferably applied to processes utilizing an alkylene oxide (epoxide) reactant which comprises one or more vicinal akylene oxides, particularly the lower alkylene oxides and more particularly those in the $C_2$ to $C_4$ range. In general, the alkylene oxides are represented by the formula

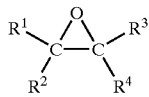

wherein each of the $R^1$, $R^2$, $R^3$ and $R^4$ moieties is individually selected from the group consisting of hydrogen and alkyl moieties. Reactants which comprise ethylene oxide, propylene oxide, or mixtures of ethylene oxide and propylene oxide are more preferred, particularly those which consist essentially of ethylene oxide and propylene oxide. Alkylene oxide reactants consisting essentially of ethylene oxide are considered most preferred from the standpoint of commercial opportunities for the practice of alkoxylation processes, and also from the standpoint of the preparation of products having narrow-range ethylene oxide adduct distributions.

Likewise, the active hydrogen containing reactants suitably utilized in the process of the invention include those known in the art for reaction with alkylene oxides and conversion to alkoxylate products. Suitable classes of active hydrogen containing reactants include (but are not necessarily limited to) alcohols, phenols, thiols (mercaptans), amines, polyols, carboxylic acids, and mixtures thereof. It is generally, but not necessarily, the case that the active hydrogen moiety of the reactant is of the form —XH wherein X represents either an oxygen, sulfur or (substituted, e.g., amino) nitrogen atom. Preference generally exists for use of hydroxyl-containing reactants. More preferably, the active hydrogen-containing reactant consists essentially of one or more active hydrogen containing compounds selected from the group consisting of alkanols, alkyl polyols and phenols (including alkyl-substituted phenols).

Preference can also be expressed for the application of this invention to the alkoxylation of primary active hydrogen containing compounds, that is, compounds wherein the active hydrogen moiety is attached to a primary carbon atom. As is often the case for alkoxylation reactions, such primary compounds are more reactive, and in some cases substantially more reactive, in the process of this invention than are the corresponding secondary and tertiary compounds. Moreover, the invention has been found to produce relatively broad-range alkylene oxide adduct distribution products when applied to secondary and tertiary active hydrogen containing reactants.

In the process to prepare the catalyst according to the invention, the active hydrogen containing organic compound should be the reactant in the alkoxylation reaction. Thus, the active rare earth catalyst is produced "in-situ" of one of the reactants.

Among the suitable carboxylic acids, particular mention may be made of the mono- and dicarboxylic acids, both aliphatic (saturated and unsaturated) and aromatic. Specific examples include lauric acid, myristic acid, palmitic acid, steric acid, oleic acid, rosin acids, tall oil acids, terephthalic acid, and the like. It has been observed that, as a rule, carboxylic acids undergo alkoxylation in the process of this invention at a relatively slow rate.

Among the suitable amines, particular mention may be made of primary, secondary and tertiary alkylamines and of alkylamines containing both amino and hydroxyl groups, e.g., N'N-di(n-butyl)-ethanol amine and tripropanolamine.

Among the suitable thiols, particular mention may be made of primary, secondary and tertiary alkane thiols having from 9 to about 30 carbon atoms, particularly those having from about 9 to 20 carbon atoms. Specific examples of suitable tertiary thiols are those having a highly branched carbon chain which are derived via hydrosulfurization of the products of the olgiomerization of lower olefins, particularly the dimers, trimers, and tetramers and pentamers of propylene and the butylenes. Secondary thiols are exemplified by the products of the hydrosulfurization of the substantially linear oligomers of ethylene as are produced by the Oxo process. Representative, but by no means limiting, examples of thiols derived from ethylene oligomers include the linear carbon chain products, such as 2-decanethiol, 3-decanethiol, 4-decanethiol, 5-decanethiol, 3-dodecanethiol, 4-decanethiol, 5-decanethiol, 3-dodecanethiol, 5-dodecanethiol, 2-hexadecanethiol, 5-hexadecanethiol, and 8-octadencanethiol, and the branched carbon chain products, such as 2-methyl-4-tridecanethiol. Primary thiols are typically prepared from terminal olefins by hydrosulfurization under free-radical conditions and include, for example, 1-dodecanethiol, 1-tetradecanethiol and 2-methyl-1-tridecanethiol.

The alcohols (both mono- and poly-hydroxy) and the phenols (including alkyl-substituted phenols) are preferred classes of active hydrogen containing reactants for purposes of the invention. Among the phenols, particular mention may be made of phenol and alkyl-substituted phenols wherein each alkyl substituent has from 3 to about 30 (preferably from 3 to about 20) carbon atoms, for example, p-hexylphenol, nonylphenol, p-decylphenol, nonylphenol, didecyl phenol and the like.

Acyclic aliphatic mono-hydric alcohols (alkanols) form a most preferred class of reactants, particularly the primary alkanols, although secondary and tertiary alkanols are also very suitably utilized in the process of the invention. Preference can also be expressed, for reason of both process performance and commercial value of the product, for alkanols having from 9 to about 30 carbon atoms, with $C_9$ to $C_{24}$ alkanols considered more preferred and $C_9$ to $C_{20}$ alkanols considered most preferred. As a general rule, the alkanols may be of branched or straight chain structure depending on the intended use. In one embodiment, preference further exists for alkanol reactants in which greater than about 50 percent, more preferably greater than about 60 percent and most preferably greater than about 70 percent of the molecules are of linear (straight chain) carbon structure. In another embodiment, preference further exists for alkanol reactants in which greater than about 50 percent, more preferably greater than about 60 percent and most preferably greater than about 70 percent of the molecules are of branched carbon structure.

The general suitability of such alkanols as reactants in alkoxylation reactions is well recognized in the art. Commercially available mixtures of primary mono-hydric alkanols prepared via the oligomerization of ethylene and the hydroformylation or oxidation and hydrolysis of the resulting higher olefins are particularly preferred. Examples of commercially available alkanol mixtures include the NEODOL Alcohols, trademark of and sold by Shell Chemical Company, including mixtures of $C_9$, $C_{10}$, and $C_{11}$ alkanols (NEODOL 91 Alcohol), mixtures of $C_{12}$ and $C_{13}$ alkanols (NEODOL 23 Alcohol), mixtures of $C_{12}$, $C_{13}$, $C_{14}$, and $C_{15}$ alkanols (NEODOL 25 Alcohol), and mixtures of $C_{14}$ and $C_{15}$ alkanols (NEODOL 45 Alcohol); the ALFOL Alcohols (ex. Vista Chemical Company), including mixtures of $C_{10}$ and $C_{12}$ alkanols (ALFOL 1012), mixtures of $C_{12}$ and $C_{14}$ alkanols (ALFOL 1214), mixtures of $C_{16}$ and $C_{18}$ alkanols (ALFOL 1618), and mixtures of $C_{16}$, $C_{18}$ and $C_{20}$ alkanols (ALFOL 1620), the EPAL Alcohols (Ethyl Chemical Company), including mixtures of $C_{10}$ and $C_{12}$ alkanols (EPAL 1012), mixtures of $C_{12}$ and $C_{14}$ alkanols (EPAL 1214), and mixtures of $C_{14}$, $C_{16}$, and $C_{18}$ alkanols (EPAL 1418), and the TERGITOL-L Alcohols (Union Carbide), including mixtures of $C_{12}$, $C_{13}$, $C_{14}$, and $C_{15}$ alkanols (TERGITOL-L 125). Also very suitable are the commercially available alkanols prepared by the reduction of naturally occurring fatty esters, for example, the CO and TA products of Proctor and Gamble Company and the TA alcohols of Ashland Oil Company.

Among the polyols, particular mentions may be made of those having from 2 to about 6 hydroxyl groups and 9 or more, preferably 9 to 30 carbon atoms. Specific examples include the alkylene glycols such as decylene glycol, the polyalkylene glycol ethers, such as tripropylene glycol, glycerine sorbitol, and the like. Higher oligomers and polymers of the polyols are also very suitable.

The active hydrogen containing reactant is also very suitably the alkoxylate product of a previous alkoxylation of an active hydrogen containing compound.

Further examples of both specific alkylene oxide reactants and specific active hydrogen containing reactants suitable for use in this invention are recited in the aforementioned U.S. Patents, the relevant disclosures of which are incorporated by this reference.

For purposes of the invention, the alkylene oxide reactant and the active hydrogen containing reactant are necessarily contacted in the presence of a catalyst comprising one or more of the phosphate salts of the rare earth elements of the invention. The catalyst is applied in an amount which is effective to catalyze the alkoxylation reaction.

In terms of processing procedures, the alkoxylation reaction in the invention may be conducted in a generally conventional manner. For example, the catalyst in the liquid active hydrogen containing reactant is contacted, preferably under agitation, with alkylene oxide reactant, which is typically introduced in gaseous form, at least for the lower alkylene oxides. Additional liquid active hydrogen containing reactant can optionally be added anytime before the addition of the alkylene oxide reactant. Thus, a concentrated catalyst reaction mixture can be made and a portion can be used as necessary.

In preferred embodiments, the alkylene oxide reactant is ethylene oxide or propylene oxide or a mixture of ethylene oxide and propylene oxide. In a further preferred embodiment, the active hydrogen containing reactant is an alcohol, a polyol or another hydroxyl containing compound. The reaction is carried out in the presence of a catalytically effective amount of the rare earth phosphate salt catalyst prepared according to the invention. In a particularly preferred embodiment, ethylene oxide is contacted and reacted with a $C_9$ to $C_{30}$ primary alkanol in the presence of a catalytically effective amount of a catalyst for aklkoxylation. Additional liquid active hydrogen containing reactant can be optionally added at any time of the process.

While these procedures describe a batch mode of operation, the invention is equally applicable to a continuous process.

Overall, the two reactants are utilized in quantities which are predetermined to yield an alkoxylate product of the desired mean or average adduct number. The average adduct number of the product is not critical to this process. Such products commonly have an average adduct number in the range from less than one to about 30 or greater.

In general terms, suitable and preferred process temperatures and pressures for purposes of this invention are the same as in conventional alkoxylation reaction between the same reactants, employing conventional catalysts. A temperature of at least about 90° C., particularly at least about 120° C., and most particularly at least about 130° C., is typically preferred from the standpoint of the rate of reaction, while a temperature less than about 250° C., particularly less than about 210° C., and most particularly less than about 190° C., is typically desirable to minimize degradation of the product. As is known in the art, the process temperature can be optimized for given reactants, taking such factors into account.

Superatmospheric pressures, e.g., pressures between about 10 and 150 psig, are preferred, with pressure being sufficient to maintain the active hydrogen containing reactant substantially in the liquid state.

When the active hydrogen containing reactant is a liquid and the alkylene oxide reactant is a vapor, alkoxylation is then suitably conducted by introducing alkylene oxide into a pressure reactor containing the liquid active hydrogen containing reactant and the catalyst. For considerations of process safety, the partial pressure of a lower alkylene oxide reactant is preferably limited, for instance, to less than about 60 psia, and/or the reactant is preferably diluted with an inert gas such as nitrogen, for instance, to a vapor phase concentration of about 50 percent or less. The reaction can, however, be safely accomplished at greater alkylene oxide concentration, greater total pressure and greater partial pressure of alkylene oxide is suitable precautions, known to the art, are taken to manage the risks of explosion. A total pressure of between about 40 and 110 psig, with an alkylene oxide partial pressure between about 15 and 60 psig, is particularly preferred, while a total pressure of between about 50 and 90 psig, with an alkylene oxide partial pressure between about 20 and 50 psig, is considered more preferred.

The time required to complete a process according to the invention is dependent both upon the degree of alkoxylation that is desired (i.e., upon the average alkylene oxide adduct number of the product) as well as upon the rate of the alkoxylation reaction (which is, in turn dependent upon temperature, catalyst quantity and nature of the reactants). A typical reaction time for preferred embodiments, particularly for when the alkylene oxide is gaseous is less than 10 hours. When ethylene oxide is used as the alkylene oxide, the typical reaction time is less than 2 hours. When propylene oxide is used as the alkylene oxide, the typical reaction time is less than 6 hours.

After the ethoxylation reaction has been completed, the product is preferably cooled. If desired, catalyst can be removed from the final product, although catalyst removal is not necessary to the process of the invention. Catalyst residues may be removed, for example, by filtration, precipitation, extraction, or the like. A number of specific chemical and physical treatment methods have been found to facilitate removal of catalyst residues from a liquid product. Such treatments include contact of the alkoxylation product with strong acids such as phosphoric and/or oxalic acids or with solid organic acids such as NAFION H+ or AMBERLITE IR 120H; contact with alkali metal carbonates and bicarbonates; contact with zeolites such as type Y zeolite or mordenite; or contact with certain clays. Typically, such treatments are followed by filtration or precipitation of the solids from the product. In many cases filtration, precipitation, centrifugation, or the like, is most efficient at elevated temperature.

Alkoxylation product mixtures prepared under the present invention are of high quality and have greater stability, relative to the product mixtures of acid or base catalyzed alkoxylation reactions. The product mixtures prepared by the method of the invention, have viscosity of about less than about 50 centipoise and is fluid. The term "fluid" means having particles which easily move and change their relative position without a separation of the mass, and which readily yield to pressure.

In this regard, the invention is particularly useful for the preparation of colorless or less colored product relative to those of conventional practice, because the neutral salts do not promote degradation reactions which lead to color forming impurities. Further, in a reaction mixture with propylene oxide, the reaction temperature is not limited to 125° C. as opposed to using a typical basic catalyst such as KOH. In the process of the invention, temperature as high as 180° C. can be used without degradation of the product.

The following Examples are provided to further illustrate certain specific aspects of the invention but are not intended to limit its broader scope.

COMPARATIVE EXAMPLE 1

A lanthanum phosphate compound was prepared by the following procedures. A first solution was prepared by dissolving 10 grams of $LaCl_3.6H_2O$ in 200 grams of deionized water. A second solution was prepared by dissolving 10.64 grams of sodium orthophosphate ($Na_3PO_4.12H_2O$) in 200 grams of water. The first solution (at room temperature) was added dropwise over a period of 25 minutes to the second solution (at 500° C.). The resulting mixture was stirred for an additional 30 minutes at 50° C., and then filtered hot to separate a white precipitate. The filter cake was washed three times with 100 ml of 50° C. deionized water. After drying, 7.4 grams of solid was recovered as a powder.

An alkoxylation process in accordance with the invention was conducted under the following procedures. The alkylene oxide reactant for this process embodiment consisted of ethylene oxide and the active hydrogen containing reactant consisted of NEODOL 23 Alcohol (NEODOL is a trademark of Shell Chemical Company) characterized as a mixture of primary, 80% linear (20% branched), alkanols having twelve and thirteen carbon atoms (about 40% by mol $C_{12}$ and 60% by mol $C_{13}$).

Initially, 3.0 grams of the powder prepared as described above was added to 200 grams of NEODOL™ 23 Alcohol, and the mixture was heated to 130° C. under nitrogen sparge for 3 hours to drive off water. The average particle size of the lanthanum phosphate compound was approximately 10 micron. The resulting slurry was transferred to a one-liter autoclave reactor maintained under nitrogen atmosphere. The temperature of the reactor and contents was raised to 140° C. A mixture of nitrogen and ethylene oxide was then introduced into the reactor to a total pressure of 75 psia (45 psia nitrogen and 30 psia ethylene oxide). Alkoxylation (ethoxylation) commenced immediately. Additional ethylene oxide was supplied on demand to maintain an essentially constant 75 psia pressure. Temperature was maintained at 140° C. A total of 315 grams of ethylene oxide was taken up over a period of 2.5 hours. The reactor was maintained for an additional hour to consume unreacted ethylene oxide in the system.

The product was waxy at room temperature and was analyzed by GC-LC techniques and found to have a mean average adduct number of 6.6. The only observed by-products were polyethylene glycols (PEG) in a quantity of 2.0% w.

EXAMPLE 1

A fluid catalyst reaction mixture was prepared according to the follow procedure. A total of 0.25 grams of lanthanum chloride hexahydrate (0.0007 moles) was added to 150 grams of NEODOL™ 23 alcohol (mixture of $C_{12}$ and $C_{13}$ having typical hydroxyl number of 289 mg/gKOH) from Shell Chemical Company (0.773 moles), and the reaction mixture was heated to 80° C. until a clear, colorless solution was produced. To this mixture was added dropwise 0.16 grams of a 42.5% w aqueous solution of phosphoric acid (0.0007 moles). The clear, colorless solution was heated to 120° C. under a nitrogen sparge to remove water until a solution containing <200 ppm $H_2O$ was obtained. This mixture was transferred to the autoclave reactor system and ethoxylated at 165° C., according to the general procedures in the previous example. A total of 238 grams (5.41 moles) of ethylene oxide was added over a 90 minute period, producing an alkanol ethoxylate having a mean average adduct number of 7.0. The product mixture was a slightly hazy, colorless fluid product with a viscosity measured at 50 cps. Viscosity was measured with a Brookfield viscosimeter.

EXAMPLE 2

A fluid catalyst reaction mixture was prepared according to the procedure described in Example 1. A total of 2.19 grams (0.0038moles) of lanthanum octanoate obtained from Rhone-Poulenc was dissolved in 166 grams (0.814 moles) of NEODOL™ 25 alcohol (mixtures of $C_{12}$, $C_{13}$, $C_{14}$ and $C_{15}$ alkanols having a typical hydroxyl number of 276 mg/gKOH) from Shell Chemical Company at 100° C. To this mixture was added dropwise 0.45 grams of an 85% w solution of phosphoric acid (0.0038 moles). After drying the catalyst mixture at 120° C. under $N_2$ sparge to a water content of <200 ppm, the reaction mixture was transferred to the autoclave system, and ethoxylated at 165° C. A total of 250 grams (5.7 moles) of ethylene oxide was added over a 120 minute period, producing an alkanol ethoxylate having a mean average adduct number of 7.0. The product mixture was a slightly hazy, colorless fluid product with a viscosity measured at 52 cps.

EXAMPLE 3

A fluid catalyst reaction mixture was prepared according to the procedure described in Example 1. A total of 17.5 grams (0.0308 moles) of lanthanum octanoate obtained from Rhone-Poulenc was dissolved in 400 grams (2.06 moles) of NEODOL™ 23 alcohol alcohol (mixture of $C_{12}$ and $C_{13}$ having typical hydroxyl number of 289 mg/gKOH) from Shell Chemical Company at 100° C. To this mixture was added dropwise 3.55 grams of an 85% w solution of phosphoric acid (0.0308 moles). After drying the catalyst mixture at 120° C. under N2 sparge to a water content of <200 ppm, the reaction mixture was transferred to a 1 gallon autoclave system. The reaction mixture was heated to 160° C., and 725 grams (16.48 moles) of ethylene oxide was added over a 45 minute period. The reaction mixture was then reacted with 1195 grams (20.6 moles) of propylene oxide at 160° C. over a 3 hour period. The reaction mixture was allowed to react for an additional 30 minutes to consume all oxide feed. The product mixture was an alkanol ethoxypropoxylate with a mean average adduct number of 8.0 moles of EO and 10 moles of PO. Analysis of the reaction product by iodine number showed no measurable olefinic substrates. There was no allyl alcohol propoxylate formed.

EXAMPLE 4

A fluid catalyst reaction mixture was prepared according to the procedure described in Example 1. A total of 3.64 grams (0.0064 moles) of lanthanum octanoate obtained from Rhone-Poulenc was dissolved in 500 mL of NEODOL™ 25 alcohol (mixtures of $C_{12}$, $C_{13}$, $C_{14}$ and $C_{15}$ alkanols having a typical hydroxyl number of 276 mg/gKOH) from Shell Chemical Company at 100° C. To this mixture was added dropwise 0.74 grams of an 85% w solution of phosphoric acid (0.0064 moles). After drying the catalyst mixture at 120° C. under $N_2$ sparge to a water content of <200 ppm, the particle size was determined to have a median diameter of 0.7 microns with standard deviation of 0.3 microns. Horiba Laser Scattering Particle Size distribution Analyzer, LA-900 was used for the determination of particle size in the range of 0.05 to 1000 microns.

I claim:

1. A process for the preparation of a fluid rare earth phosphate catalyst composition comprising:
   a) providing a rare earth salt soluble in $C_9$–$C_{30}$ active hydrogen containing organic compound at a temperature of less than 120° C.;
   b) adding and dissolving the rare earth salt in a $C_9$–$C_{30}$ active hydrogen containing organic compound thereby producing a rare earth/organic solution; and
   c) adding phosphoric acid to the rare earth/organic solution in a rare earth to phosphoric acid molar ratio in the range of 0.7:1 to 1.3:1 thereby producing the fluid rare earth phosphate catalyst composition.

2. The process of claim 1 wherein the molar ratio of rare earth to phosphoric acid is in the range of 0.9:1 to 1.1:1.

3. The process of claim 1 wherein the phosphoric acid is a phosphoric acid solution in a concentration in the range of 50 weight percent to 85 weight percent in water.

4. The process of claim 1 wherein the rare earth salt comprises a lanthanum salt.

5. The process of claim 4 wherein the lanthanum salt is selected from the group consisting of halides, nitrates, and carboxylates.

6. The process of claim 5 wherein the phosphoric acid is a phosphoric acid solution in a concentration in the range of 50 weight percent to 85 weight percent in water.

7. The process of claim 1 further comprising adding a base that does not contain a Group 1 or Group 2 of the elements of the periodic table in an amount effective to adjust the pH of the composition to a pH in the range of 5 to 8.

8. The process of claim 7 wherein the base is ammonium hydroxide.

9. The process of claim 1 wherein the active hydrogen containing compound is a $C_9$–$C_{30}$ primary mono-hydric alkanol or alkylphenol.

10. The process of claim 9 wherein the active hydrogen containing compound is a $C_9$–$C_{30}$ primary mono-hydric alkanol.

11. The process of claim 10 wherein the active hydrogen containing compound is a mixture of $C_9$ and $C_{20}$ alkanols.

* * * * *